United States Patent [19]

Heyden

[11] Patent Number: 4,772,260
[45] Date of Patent: Sep. 20, 1988

[54] RECTAL CATHETER

[76] Inventor: Eugene L. Heyden, S. 627 Bernard #8, Spokane, Wash. 99204

[21] Appl. No.: 858,799

[22] Filed: May 2, 1986

[51] Int. Cl.$^4$ ............................................. A61M 25/00
[52] U.S. Cl. ...................................... 604/45; 604/96; 604/129; 604/269
[58] Field of Search .................... 604/41–42, 604/45, 96–104, 128–129, 269

[56] References Cited

U.S. PATENT DOCUMENTS

| | | | |
|---|---|---|---|
| 724,913 | 4/1903 | Montgomery | 604/278 |
| 1,902,418 | 3/1933 | Pilgrim | 604/43 |
| 2,667,682 | 2/1954 | Stone | 604/45 X |
| 2,930,378 | 3/1960 | Buyers | 604/45 |
| 3,114,373 | 12/1963 | Andersen | 604/45 |
| 3,429,314 | 2/1969 | Ericson | 604/129 |
| 3,459,175 | 8/1969 | Miller | 604/104 X |
| 3,460,541 | 8/1969 | Doherty | 128/207.15 |
| 3,542,031 | 11/1970 | Taylor | 604/269 X |
| 3,802,418 | 4/1974 | Clayton | 128/749 |
| 4,690,672 | 9/1987 | Veltrup | 604/43 |

OTHER PUBLICATIONS

Lancet, "New Inventions", Oct. 29, 1955, p. 908.

Primary Examiner—Dalton L. Truluck

[57] ABSTRACT

Particularly a rectal catheter for the removal of fluent material from the rectal cavity. The rectal catheter (18) comprises an elongated tubular member (20) forwardly insertable within the rectal cavity. The tubular member includes a pair of opposing eyelets (28a and 28b) in the vicinity of a forward end (22) which lead to a centrally open drainage lumen (26), and also includes a ventilation lumen (32) substantially coextensive in length therewith. The ventilation lumen receives atmospheric air from a take-off tube (40) depending from the rearward portion of the tubular member and directs atmospheric air toward the forward end of the tubular member when suction is applied to the drainage lumen. Accordingly, the ventilation lumen is terminated at the forward end of the tubular member and presents a venting aperture (36) radially and inwardly offset from the ventilation lumen, positioned in the vicinity of the base of the eyelets, and directed toward the direction of the rearward end (24) of the tubular member. When suction is applied to the catheter, a directional reversal of atmospheric air is seen as it is conducted through the ventilation lumen in a forward direction, drawn through the venting aperture and into the drainage lumen, and directed toward the suction source and rearward end of the tubular member. A novel, conically shaped retaining member (44, 44', and 44") is described and contemplated as a particularly suitable alternative to an expansible cuff (76).

18 Claims, 4 Drawing Sheets

RECTAL CATHETER

TECHNICAL FIELD

This invention relates to medical devices in general, and more particularly to tubular devices used in the introduction and/or removal of fluent material from a body cavity such as the rectum. Representative of such devices are Miller, U.S. Pat. No. 3,459,174 and Mattler, U.S. Pat. No. 3,896,816.

BACKGROUND ART

Of particular concern in the clinical setting is the problem of diarrhea in the physically ailing or compromised patient. In the incontinent patient, this problem can lead to skin irritation and breakdown, as well as to increased cost of patient care from a material and time utilization standpoint. In certain medical situations, episodes of diarrhea can last continuously for days, or intermittently for weeks. Not only fecal material, but other fluent material, such as hemorrhagic fluid from a GI bleed, can lead to significant problems for both patient and health care worker. Drainage devices ranging from adhesively attached external pouches to enema devices and large-sized Foley-type cathethers, all of which rely upon hydraulic forces or gravity to achieve drainage, have been used and suggested in address of the problem. Ineffective drainage and leakage around such prior art apparatus is a common occurrence.

It is therefore one object of the present invention to provide a drainage device having improved drainage of fluent material. It is another object of the present invention to provide a drainage device of a character which discourages leakage of material around the outside of the device. It is yet another object of the present invention to provide a drainage device safely operable by suction. These and other objects will become apparent from an understanding of the present invention.

DISCLOSURE OF THE INVENTION

The present invention provides a rectal catheter which is admissible within the rectal cavity of a patient and provides for the drainage of substantially fluent material therefrom. In the preferred embodiment a simply constructed drainage catheter is disclosed which includes an elongated tubular member for forward insertion within the rectal cavity and rearwardly connectable to a drainage hose, a drainage lumen defined by said tubular member, a ventilation system including a forwardly disposed venting aperture strategically placed and directed toward the contemplated direction of flow for fluent material, and a conically shaped retaining member particularly suitable for its use in providing for both the retention of the catheter and a seal with the floor of the rectum. Of particular advantage is the opportunity to encourage the drainage of material through the device by applying suction to the rearward end thereof, and to do so without the risk that negative pressure will build up within the rectal cavity or the risk that suction entrapment of rectal tissue by the device will occur.

In operation, and particularly when suction is applied to the catheter, substantially fluent material delivered by gravity or peristalsis to an area within the catheter near the venting aperture is promptly transported through the catheter and out the same, to be collected in a canister trap for measurement and disposal. It is with specific intent that the venting aperture is placed near the area of the catheter where suction exerts its strongest influence on the rectal cavity and is directed toward the intended direction of flow for fluent material. In such a relation, a forward flow of atmospheric air through the ventilating lumen can continue at a time when fluent material is flowing past the venting aperture in a rearward direction, thereby limiting the occurrence of material entering and draining out the ventilating lumen and preventing a negative pressure build-up from occurring within the rectal cavity.

BRIEF DESCRIPTION OF THE DRAWING

The invention can best be understood in conjunction with the accompanying drawing to which the description of the preferred embodiment corresponds.

BEST MODE FOR CARRYING OUT THE INVENTION

Referring now to the drawing, and more particularly to FIGS. 1 through 6 which illustrate the distinctive features of the invention in the preferred embodiment, the rectal catheter 18 comprises a centrally open and generally tubular device of elastomer material such as a latex, constructed, as it were, about a central axis. Comprising largely of an elongated tubular member 20 including a forward end 22 for insertion within the rectal cavity and an opposing rearward end 24 for residing a distance outside the patient, the rectal catheter 18 further comprises a ventilation system and a conically shaped member for retaining the catheter within the rectal cavity and for seating with the floor of the same, as will be discussed in greater detail as the disclosure unfolds.

Figures 1, 2, 3:
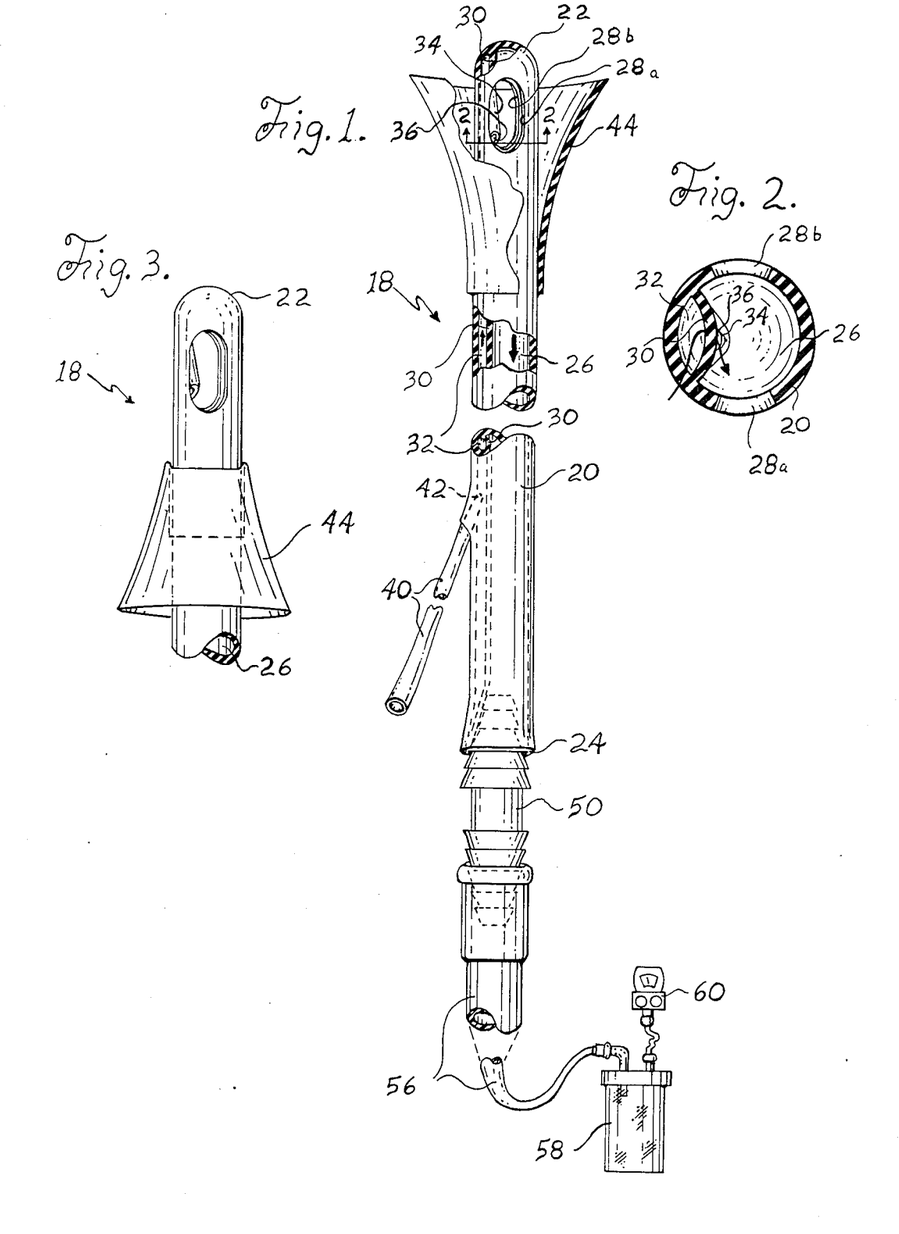
FIG. 1 is a perspective view of the preferred embodiment of the invention, cut away and sectioned for purposes of illustration and illustrated in conjunction with an associating collection system having suction-force capability.
FIG. 2 is an enlarged cross-sectional view taken from the line 2—2 of FIG. 1.
FIG. 3 portionally illustrates the preferred embodiment of the invention, showing a directional reversal of a conically-shaped retaining member.

Referring particularly to FIG. 1, the tubular member 20 is shown connected at its rearward end 24 to a drainage hose 56 by means of a pipecone adapter 50. The drainage hose 56 feeds into a collection canister 58 which, in turn, is connected to a suction control unit 60 such as is commonly available at the patient bedside. A suitable degree of suction would be on the order of 60 to 120 mmHg. Although the rectal catheter will function as a drain without the use of applied suction, it is advantageous that suction be applied thereto to provide prompt removal of fluent material arriving at the catheter, preventing any build up of material which could cause leakage around the catheter and providing for the removal of fluent material of a relatively high viscosity.

Again referring to the preferred embodiment of the invention, particularly illustrated in FIG. 1, it is seen that a ventilation lumen 32 resides alongside a drainage lumen 26 and exists centrally open a substantial length of the tubular member 20. Radially offset from the central axis of the tubular member 20 and separated from the drainage lumen 26 by an interluminal wall 30, the ventilation lumen 32 terminates at the forward end 22 of the tubular member and is closed to the region beyond the catheter by a joining of the interluminal wall and the tubular member proper. The closure of the ventilation lumen 32 serves to prevent fluid communication between the ventilation lumen and the rectal cavity at the forward end 22 of the tubular member and to allow atmospheric air to be directed toward a venting aperture 36 provided internally within the forward portion of the tubular member. At a rearward location along the tubular member is placed a centrally open take-off tube 40 exiting therefrom, having had its forward end 42 inserted to reside a distance within the ventilation lumen 32. The take-off tube 40 allows atmospheric air to enter the ventilation lumen 32 and to continue in a flow path directed initally toward the forward end 22 of the tubular member. The take-off tube 40 is preferably left open to atmospheric air but may be clamped off or occluded to prevent drainage to occur therethrough, such as may occur when suction is not applied to the catheter or at a time when material such a barium is injected into the rectal cavity through the drainage lumen. Additionally, a syringe (not shown) may be attached to the take-off tube 40 and used to periodically irrigate the ventilation system with a suitable irrigating solution to keep it free from material build-up or to remove a blockage.

Proceeding further in the description of the invention in the preferred embodiment, opposing eyelets 28a and 28b are provided in the vicinity of the forward end 22 of the tubular member 20 in order to establish fluid communication between the drainage lumen 26 and the rectal cavity and to establish an inlet for fluent material to enter within the drainage lumen. Accordingly, the direction of flow of fluent material outward from the rectal cavity would be through the eyelets 28a and 28b, into and along the drainage lumen 26, past the rearward end 24 of the tubular member, and toward the collection canister 58. As previously pointed out, the use of suction is contemplated in the transport of fluent material through the catheter. In the event that one eyelet should come in contact with the wall of the rectal cavity or with an inner wall of the conically-shaped retaining member 44, the other eyelet will be available for receiving fluent material. It should also be noted, that if for some unforseen reason, such as abnormal anatomy, both eyelets should come in contact with rectal tissue, it can be readily appreciated that suction will not negatively act thereupon, as the negative pressure generated thereby is vented near the base of the eyelets and not allowed to build up within the rectal cavity or exert an appreciable influence on rectal tissue. Additionally, a degree of isolation of the eyelets from the rectal tissue is afforded by their location deep within the conically-shaped retaining member, further protecting the rectal tissue from potential suction entrapment.

Referring now particularly to FIG. 1 and the cross section thereof from the line 2—2 illustrated in FIG. 2, the nature of the ventilation system according to the present invention is illustrated. Arrows incorporated with the illustrations depict the flow path intended at various locations within the catheter during the operation of the device. As previously pointed out, and when suction is applied to the catheter, atmospheric air is drawn into the ventilation lumen 32 through the take-off tube 40 and conducted toward the forward end 22 of the catheter to relieve the negative pressure exposed to the rectal cavity. Near the forward end 22 of the tubular member a longitudinally extending inward projection 34 of the interluminal wall 30 angularly extending within the drainage lumen 26 from a location in the vicinity of the catheter until it structurally provides for the venting aperture 36 in a manner which faces the venting aperture in the direction of the rearward end 24 of the tubular member. Accordingly, the venting aperture 36 is directed toward the flow direction defined and intended by the drainage lumen 26 and is located in the vicinity of the base of the eyelets 28a and 28b, a location where suction is strongest in influence on the area between the eyelets and on the rectal cavity. In FIG. 1 both the inward projection of the interluminal wall 34 and the venting aperture 36 are clearly seen through eyelet 28a. In FIG. 2 the arrow illustrates the directional reversal of atmospheric air as it is drawn from the ventilating lumen 32, through the venting aperture 36, into the drainage lumen 26, and out the same via drainage hose 56. It can readily be appreciated that the ventilation system will limit the build up of negative pressure within the rectal cavity by the circulation of atmospheric air through the device. It can also be reaily appreciated that substantially fluent material presenting to the catheter by gravity or peristalsis will enter the eyelets and be promptly transported out of the rectal cavity through the drainage lumen 26 of the catheter. It should be noted, however, that during times when pressures within the rectal cavity are such that fluent material is presented to the drainage lumen in excess of that which can promptly be removed by suction, fluent material may be temporarily forced a distance within the ventilation lumen 32 until such time that negative pressure is again exerted upon the ventilation lumen, clearing the same from entertained fluent material.

Referring now particularly to FIGS. 1 and 3, the nature of the conically-shaped retaining member 44, provided for retaining the catheter within the rectal cavity and for sealing with the floor of the same, is clearly illustrated. Attached to the tubular member at its conically smallest portion, the retaining member 44 resembles a cone which is conically largest in the vicinity of the forward end 22 of the tubular member 20. The retaining member is of a wall thickness which allows it to be both substantially shape-retaining and flexible, lending to the same a degree of flexibility in order to achieve an inversion and directional reversal, as illustrated in FIG. 3. In the illustration of FIG. 3, the forward portion of the tubular member, having the conically-shaped retaining member 44 inverted and reversed in direction, is shown as it would appear prior to insertion of the catheter within the rectal cavity. In such a position, the steps for the insertion and positioning of the device, as detailed in FIGS. 4, 5, and 6, can be carried out.

Figures 4, 5, 6:
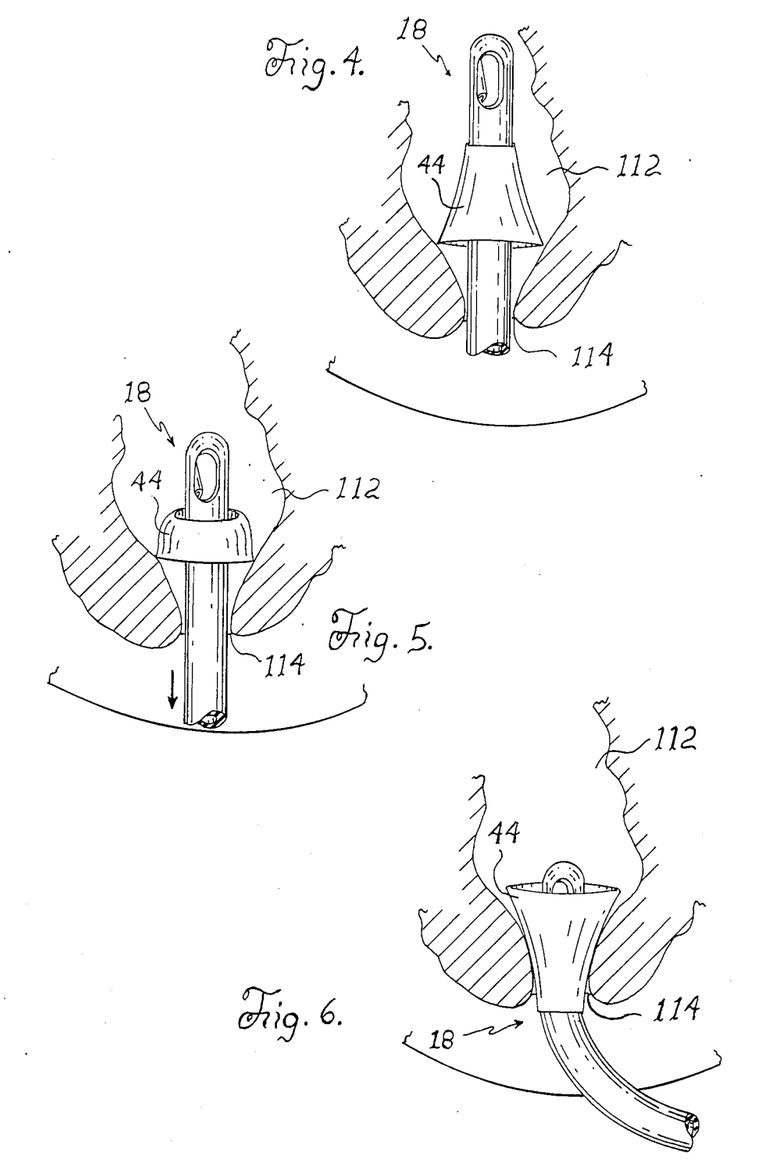
FIGS. 4, 5, and 6 illustrate the preferred embodiment of the invention in a sequence that details the installation of the catheter within the rectal cavity.

Prior to the insertion of the device, as illustrated in the FIGS. 4 through 6, a suitable lubricating agent should be applied to the forward portion of catheter for ease of insertion. Experience has shown that a rotating of the catheter would be beneficial during its insertion, an action which would cause the remaining member 44 to fold upon itself into a somewhat longitudinally-extending fold or pleat, lessening the diameter thereof and providing for an additional ease of insertion.

Referring now to the installation sequence in the drawings, FIG. 4 shows the catheter inserted within the rectal cavity 112 a distance sufficient to free the inverted conically-shaped retaining member 44 from the anal sphincter 114. The rectal catheter 18 is then withdrawn in an action which reverses the inverted state of the conically-shaped retaining member 44, as illustrated in FIG. 5. The catheter is then withdrawn in an action which completes the reversal of the retaining member and seats the same with the floor of the rectal cavity, as illustrated in FIG. 6. The reversal of the conically-shaped retaining member resembles a roll-sock action as its conically largest portion abuts with the floor of the rectal cavity and forces the retaining member out of its inverted state in a roll-like progression while the catheter is withdrawn into a seated position with the floor of the rectal cavity. The flexibility of the retaining member also allows a degree of conformance with the contour of the floor of the rectal cavity, adding to the sealing function of the conically-shaped retaining member.

The flexibility of the conically-shaped retaining member again comes into play when the catheter is removed from the rectal cavity. When a suitable degree of traction is applied to the catheter, it will be seen that the greater diameter of the retaining member will decrease in size somewhat as tension and compression is exerted thereupon as it passes through a restrictive anal sphincter. One, or a plurality of longitudinally extending folds or pleats may also be formed in the retaining member as it withdraws through the anal sphincter, further easing the removal of the catheter from within the patient by decreasing the greater diameter of said conically-shaped retaining member.

The basic principles of the invention as demonstrated in the preferred embodiment give rise to variations equally within the scope of the present invention.

Figure 7:
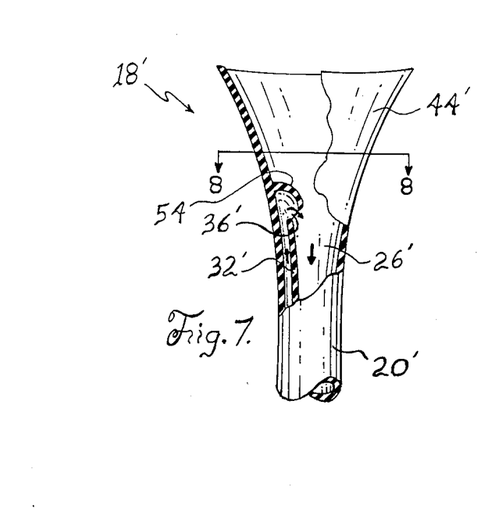
FIG. 7 is a persepective view of an alternative embodiment of the invention.
Figure 8:
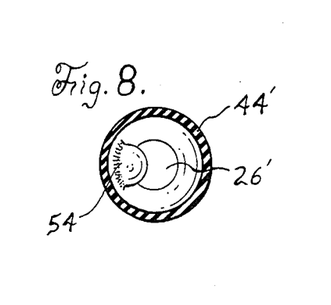
FIG. 8 is a cross section taken from the line 8—8 of FIG. 7.

FIG. 7, together with the line 8—8 cross section thereof illustrated in FIG. 8, demonstrates an alternative embodiment of the invention. In this embodiment, the ventilation system of the rectal catheter 18', including a ventilation lumen 32' defined by an elongated tubular member 20' and venting aperture 36', is substantially identical to the same of the preferred embodiment. (The rearward portion of the catheter is not shown but is to be considered as substantially identical in character with its counterpart as illustrated in FIG. 1.) As in the preferred embodiment, arrows incorporated in the drawing show flow paths substantially identical with the embodiment of FIG. 1, and the use of suction and a suction collection system is contemplated during the operation of the invention in this alternative embodiment. In FIG. 7, and in the cross-sectional view in FIG. 8, a cap-like projection 54 of the retaining member 44' is illustrated and contributes to the structural provision for the venting aperture 36' and serves to direct atmospheric air toward the flow path of the drainage lumen 26', in counterpart with the inward projection 34 of the preferred embodiment. The conically-shaped retaining member 44' inverts, acts, and functions the same as seen in FIGS. 3 through 6. In variation with the preferred embodiment, however, the projection of the tubular member beyond the base of the conically-shaped retaining member 44' is not seen. Eyelets are also absent in this embodiment, and the conically-shaped retaining member 44' serves entirely as a fluid-communicating inlet to the drainage lumen 26'. Indeed, in this form of the invention, the retaining member 44' could be considered to be coaxial and to be a progressively enlarging continuation of the tubular member. It can be appreciated that the ventilation system of the catheter, as well as both the distance between the conically largest portion of the retaining member and the area near the venting aperture where suction exerts its strongest influence on the rectal cavity, will prevent the occurrence of suction entrapment of rectal tissue by the device.

Figure 9:
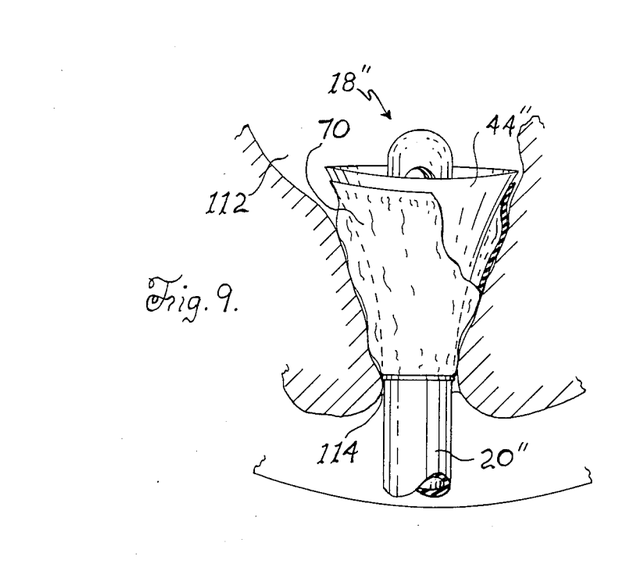
FIG. 9 is a perspective view of the invention in yet another embodiment.

FIG. 9 illustrates another alternate embodiment of the invention, particularly pointing out an additional feature within the scope of the invention. In this figure, a conically shaped cuff 70 is attached at opposing ends to the conically-shaped retaining member 44'' of the rectal catheter 18''. The conically-shaped cuff 70 is partially cut away to illustrate its relatively thin-walled nature. Though an inflation means incorporated within the catheter and in communication with the interior of the conically-shaped cuff would be in accordance with the present invention, a fixed volume of air entrapped between the inner wall of the conically-shaped cuff 70 and the outer wall of the conically-shaped retaining member 44'' is contemplated and serves to continuously maintain the conically-shaped cuff in a partially inflated condition. As in previously described embodiments of the invention, the conically-shaped retaining member 44'' inverts and re-extends for a respective insertion and positioning of the catheter; however, in this embodiment, it is the conically-shaped cuff 70 rather than the outer wall of the retaining member that seats with the floor of the rectal cavity 112 as the retaining member resides in a dependent relation therewith. When the retaining member is inverted prior to insertion within the rectal cavity, it will be seen that the conically-shaped cuff 70 is directionally reversed and maintained between the retaining member and the tubular member 20'' of the catheter until such time as the retaining member 44'' is again extended in its forwardly extending position. The function of the conically-shaped cuff is to provide an improved seal with the floor of the rectal cavity by utilizing a cushion of air to support it against said floor in a closely conforming attitude with surface irregularities of the same.

Figures 10, 11, 12:
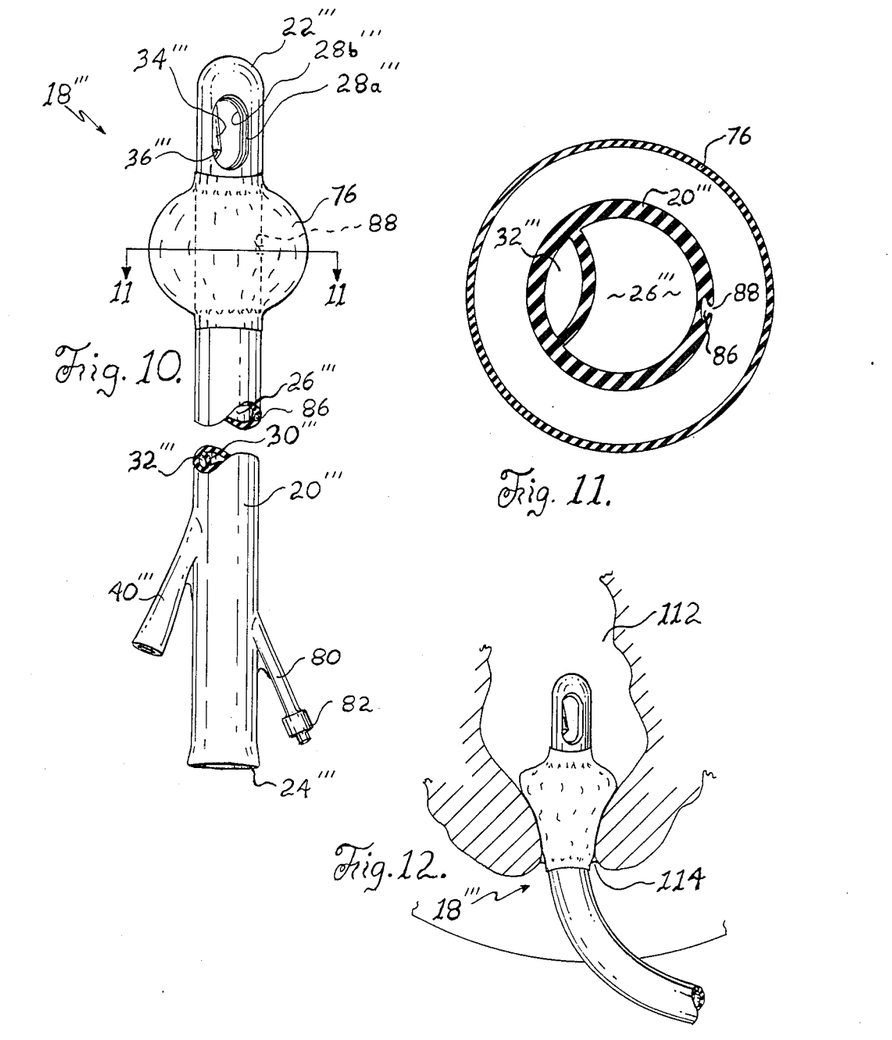
FIG. 10 is a perspective view of an alternative embodiment also within the scope of the present invention.
FIG. 11 is a cross section taken from the line 11—11 of FIG. 10.
FIG. 12 illustrates the alternative embodiment of FIG. 10 as it would appear inserted and functionally positioned within the patient.

FIGS. 10, 11, and 12 teach yet another embodiment of the invention. To be understood in conjunction with the illustrations of the preferred embodiment in FIGS. 1 and 2, this embodiment differs principally with respect to the means contemplated for retaining the catheter within the rectal cavity. The rectal catheter 18''' of this embodiment includes a tubular member 20''' having a forward end 22''' and an opposing rearward end 24''', a drainage lumen 26''' and ventilation lumen 32''', together with a pair of eyelets 28a''' and 28b''' and other members in similarity with the preferred embodiment, such as a take-off tube 40'''. An inward projection 34''' of the interluminal wall 30''', together with a venting aperture 36''', is also present, as illustrated in the preferred embodiment. In this embodiment, however, an expansible cuff 76 coaxially is carried on the tubular member 20''' below and in the vicinity of the eyelets, replacing the conically-shaped retaining member of the preferred embodiment. Associated with the expansible cuff 76 is a cuff inflation system for inflating, sustaining inflation, and deflating the cuff. The cuff inflation system contemplated is well known in the art and includes a check valve 82, a hollow stem 80 leading to a cuff inflation lumen 86 formed within the wall of the tubular member, and a cuff inflation opening 88 forming communication between the interior of the cuff and the cuff inflation lumen. As a gas or a liquid is injected within or withdrawn from the cuff inflation system, it passes through a cuff inflation opening and expands or deflates the cuff. The cuff, like the conically-shaped retaining member of previous embodiments, serves to retain the catheter within the rectal cavity and seat with the cavity floor. Details of the cuff inflation system are particularly evident in the cross section in FIG. 11 taken from the line 11—11 of FIG. 10. FIG. 12 illustrates the rectal catheter 18''' according to this embodiment of the invention, having its cuff 76 inflated and positioned dependently within the rectal cavity 112.

CONCLUSION

From the foregoing, it is clearly evident that the present invention can be of several embodiments. Though presented in its preferred form and in selected variations, it is to be understood that the practice of other variations obvious to the principles herein set fourth would be in keeping with the spirit and scope of the invention. It is also to be understood that additional elements common to the art, such as the externally remaining abutment element according to Miller, U.S. Pat. No. 3,459,175, could be added in the practice of the invention. It is readily appreciable that the technology for manufacturing the present invention is well known and that the nature of the ventilation system allows the catheter to be easily removed from a mold, should an injection molding technique be used.

Though suggested primarily for use with the incontinent patient, it is also to be understood that the invention has usefulness in other clinical situations. For example, the device can be used to introduce and/or remove fluent material from the colon or illium through an ostomy formation. The device may also be used as a surgical drain for removing exudate from a wound or surgical field, and may be used as such with or without the use of suction. Though principally for use in venting a closed cavity, the ventilation system may also be used as an irrigation system for flushing the cavity or for irrigating the drainage lumen of the catheter to keep it free from material build up. Also, naso-gastric tubes would benefit from the ventilation system of the present invention, since back up of fluent material in a ventilation lumen, as well as ineffective drainage of fluent material by the device, is commonplace.

In keeping with the foregoing, what is claimed is:

1. A drainage device for insertion within an anatomical cavity and operable by suction for the removal of fluent material from said cavity, comprising:

an elongated tubular member of flexible material and including a forward portion and forward end adapted for insertion within an anatomical cavity and a rearward portion and rearward end provided for residing outside said anatomical cavity, said tubular member presenting a longitudinal axis and defining a centrally open drainage lumen means leading from said rearward end to an apertured fluid communication means defined by said tubular member, said an apertured fluid communication means located in the vicinity of said forward end for providing fluid communication between said anatomical cavity and said drainage lumen means and for serving as an inlet for fluent material to enter within said drainage lumen means; and a ventilation system defined by said drainage device for venting negative pressure exposed to said anatomical cavity at said an apertured fluid communication means by the application of suction of said drainage lumen means at a location in the vicinity of said rearward end, said ventilation system comprising a ventilation lumen means internally defined by said tubular member and residing alongside said drainage lumen means, said ventilation lumen means provided for conducting atmospheric air from a region outside said anatomical cavity in a direction toward said forward end and to a location in the vicinity of said an apertured fluid communication means, re-directing means associated with said ventilation lumen means and defined within said tubular member for re-directioning atmospheric air in a direction generally away from said forward end, and a venting aperture means associated defined by said re-directioning means and adapted for exiting atmospheric air in a generally rearward direction at a location substantially within and enclosed by said drainage lumen means and in the vicinity of said fluid communication means, said air re-directioning means comprising an inwardly projecting wall member means projecting within said drainage means and substantially located between said drainage lumen means and said ventilation lumen means, said wall member means of longitudinal extent having a substantial portion extending angularly within said drainage lumen means and residing between said venting aperture means and said forward end.

2. The device according to claim 1, wherein said apertured fluid communication means comprises at least one eyelet defined by said tubular member and positioned laterally with respect to said longitudinal axis.

3. The device according to claim 1, wherein said apertured fluid communication means comprises at least two substantially opposing eyelets defined by said tubular member and positioned laterally with respect to said longitudinal axis.

4. The device according to claim 1, wherein said apertured fluid communication means is substantially coaxial with respect to the longitudinal axis of said tubular member and is defined at said forward end.

5. The device according to claim 1, wherein said inwardly projecting wall member means is of longitudinal extent and comprises a portion of an interluminal wall means residing between said venting aperture means and said forward end.

6. The device according to claim 5, wherein said ventilation lumen means is occluded by occlusion means defined a predetermined distance forward said venting aperture means, said occlusion means provided for preventing fluid communication between said ventilation lumen means and said anatomical cavity at the forward end of said tubular member.

7. The device according to claim 1, wherein said ventilation lumen means is associated with a take-off tube means centrally open and projecting laterally from said tubular member and the longitudinal axis thereof, said take-off tube means adapted to receive atmospheric air and conduct the same to a location within said ventilation lumen means for passage toward said venting aperture means.

8. The device according to claim 1, wherein said tubular member carries a retaining means at a location in the vicinity of said apertured fluid communication means in an arrangement whereby said retaining means is substantially coaxial with respect to the longitudinal axis of said tubular member and is adapted to retain the forward portion of said tubular member within said anatomical cavity.

9. The device according to claim 8, wherein said retaining means comprises a conically shaped retaining member of flexible material that includes a conically smallest portion extending from a fixed location on said tubular member and a conically largest portion free for movement with respect to said tubular member, said conically-shaped retaining member progressively extending away from said tubular member in the vicinity of said fluid communication means in an extended first position;

whereby said conically-shaped retaining member is adapted to invert and reverse in direction to a range of positions wherein said conically largest portion faces in the direction of the rearward end of said tubular member in preparation for the insertion of said tubular member a satisfactory distance within said anatomical cavity, and said conically-shaped retaining member is adapted to re-extend to again achieve said first position when said conically largest portion is forced out of its reversed state by an urging of the same in a forward direction against the floor of said anatomical cavity by an action which withdraws said tubular member a satisfactory distance away from said anatomical cavity.

10. The device according to claim 9, wherein the forward portion of said tubular member and said apertured fluid communication means extend a predetermined distance beyond the conically smallest portion of said conically-shaped retaining member.

11. The device according to claim 10, wherein said apertured fluid communication means resides between the conically smallest portion of said conically-shaped retaining member and the forward end of said tubular member.

12. The device according to claim 9, wherein a cuff means carried by said tubular member encloses a space between said conically-shaped member and said cuff means, said cuff means residing on the outside of said conically-shaped member when said conically-shaped member is in said extended first position.

13. The device according to claim 8, wherein said tubular element extends a predetermined distance beyond said retaining means, wherein said retaining means comprises a inflatable cuff carried upon said tubular member in the vicinity of said forward end and in a position along said tubular member which is rearward with respect to said apertured fluid communication means, and wherein said tubular member includes a cuff inflation lumen means in fluid communication with the interior of said cuff.

14. A ventilation system included in the construction of a tubular medical device adapted for insertion within an anatomical cavity for the purpose of removing substantially fluent material from said anatomical cavity by the application of suction to a centrally open drainage lumen means defined by a tubular member, said tubular member including a forward portion and forward end adapted for insertion within said anatomical cavity, and a rearward portion and rearward end residing outside said anatomical cavity when said forward portion resides a satisfactory distance therein, said tubular member also defining a longitudinal axis and an apertured fluid communication means for providing fluid communication between said anatomical cavity and said drainage lumen means, said fluid communication means residing in the forward portion of said tubular member, the ventilation system comprising:

a ventilation lumen means defined by said tubular member and residing alongside said drainage lumen means for conducting atmospheric air from a region outside said anatomical cavity in a direction toward said forward end and to a location in the vicinity of said fluid communication means, air re-directioning means in association with said ventilation lumen means and defined within and enclosed by said tubular member for re-directioning atmospheric air in a direction generally away from said forward end, and a venting aperture means located at the bottom of said air re-directioning means adapted for exiting atmospheric air in a generally rearward direction at a location substantially within said drainage lumen means and in the vicinity of said fluid communication means, said air-re-directioning means comprising an inwardly projecting wall member means projecting within said drainage lumen means and substantially located between said drainage lumen means and said ventilation lumen means, said wall member means of longitudinal extent having a substantial portion extending angularly within said drainage lumen means and residing between said venting aperture means and said forward end.

15. The ventilation system as defined in claim 14, wherein an occlusion means for occluding said ventilation lumen means at said forward end is defined beyond said apertured fluid communication means a distance forward the same, said occlusion means closing said ventilation lumen means to forward communication with said anatomical cavity.

16. The ventilation system as defined in claim 14, wherein said ventilation lumen means is defined within the wall of said tubular member, wherein said ventilation lumen means is associated with a take-off tube means centrally open and projecting laterally away from said tubular member and the longitudinal axis thereof, and wherein said take-off tube means is adapted to receive atmospheric air and conduct the same to a location within said ventilation lumen means.

17. The ventilation system as defined in claim 14, wherein said ventilation lumen means leads to a conically shaped retaining member carried by said tubular member at the forward end thereof, and said air-reconditioning means is carried on said conically-shaped retaining member at an internal location.

18. In a drainage device which includes a tubular member defining a centrally open drainage lumen means for providing a flow path for fluent material directionally away from an apertured fluid communication means defined by a forward portion of said tubular member and directionally toward a rearward end of said tubular member, and wherein said drainage device presents a ventilation lumen means residing alongside said drainage lumen means for conducting atmospheric air from a location in the vicinity of said rearward end to a location in the vicinity of said apertured fluid communication means, and also presents an interluminal wall means defined between said drainage lumen means and said ventilation lumen means, the improvement comprising:

air re-directioning means in association with said ventilation lumen means and defined within and enclosed by said tubular member for re-directioning atmospheric air and exiting said air within said drainage lumen means, generally in the direction of said flow path, and located in the vicinity of said apertured fluid communication means, said air re-directioning means located within the vicinity of said apertured fluid communication means and comprising an angularly projecting portion of said intraluminal wall means projecting within said drainage lumen means defining at its terminus a ventilation aperture means projecting portion of said interluminal wall means adapted to project within said drainage lumen means and define a ventilation aperature means.

* * * * *

UNITED STATES PATENT AND TRADEMARK OFFICE
CERTIFICATE OF CORRECTION

PATENT NO. : 4,772,260

DATED : Sep. 20, 1988

INVENTOR(S) : Eugene L. Heyden

It is certified that error appears in the above-identified patent and that said Letters Patent is hereby corrected as shown below:

Col. 2, line 51, "central" should be --longitudinal--.
      line 63, "pipecone" should be --pinecone--.
Col. 3, lines 11 and 12, "central" should be --longitudinal--.
      line 43, after "opposing" insert --apertures or--.
Col. 4, line 66, after "to" insert --the--.
Col. 5, line 8, "remaining" should be --retaining--.
Col. 6, line 62, after "of" insert --opposing apertures or--.
Col. 7, line 36, place a period after known and delete lines 37, 38 and 39.
Col. 8, line 2, delete "an".
      line 10, delete "an".
      line 20, delete "an".
      line 30, after "said" insert --apertured--.
Col. 9, line 55, "element" should be --member--.

Signed and Sealed this

Fourth Day of April, 1989

Attest:

DONALD J. QUIGG

*Attesting Officer*

*Commissioner of Patents and Trademarks*